United States Patent
Izzo et al.

(10) Patent No.: US 8,562,388 B2
(45) Date of Patent: Oct. 22, 2013

(54) MASTECTOMY PROSTHESIS AND BRA

(75) Inventors: John Izzo, Vimont (CA); Sarah Giroux, Vimont (CA); Christine Harding, Saint-Laurent (CA)

(73) Assignee: La Vie en Rose, Montreal QC (CA)

( * ) Notice: Subject to any disclaimer, the term of this patent is extended or adjusted under 35 U.S.C. 154(b) by 590 days.

(21) Appl. No.: 12/646,613

(22) Filed: Dec. 23, 2009

(65) Prior Publication Data

US 2011/0153016 A1     Jun. 23, 2011

(51) Int. Cl.
*A41C 3/00*     (2006.01)

(52) U.S. Cl.
USPC .................................. 450/57; 450/54; 2/267

(58) Field of Classification Search
USPC ................ 450/36–39, 54–58, 1; 2/267, 268; 623/7, 8
See application file for complete search history.

(56) References Cited

U.S. PATENT DOCUMENTS

| | | | |
|---|---|---|---|
| 3,681,787 A * | 8/1972 | Perras | 623/8 |
| 3,701,168 A | 10/1972 | Balow | |
| 3,795,921 A * | 3/1974 | Zucker | 623/7 |
| 3,845,507 A * | 11/1974 | Kirby et al. | 623/7 |
| 3,896,506 A | 7/1975 | Hankin et al. | |
| 3,934,274 A * | 1/1976 | Hartley, Jr. | 623/8 |
| 4,023,575 A | 5/1977 | Nixon | |
| 4,071,914 A | 2/1978 | Silverman | |
| 4,125,117 A * | 11/1978 | Lee | 450/57 |
| 4,676,795 A | 6/1987 | Grundei | |
| 4,795,464 A * | 1/1989 | Eberl et al. | 623/8 |
| 4,828,559 A | 5/1989 | Greenberg | |
| 5,098,330 A * | 3/1992 | Greenberg | 450/55 |
| 5,395,280 A | 3/1995 | Greenberg | |
| 5,607,473 A * | 3/1997 | Weber-Unger et al. | 623/8 |
| 5,782,671 A * | 7/1998 | Suen et al. | 450/38 |
| 6,101,630 A * | 8/2000 | Lee | 2/57 |
| 6,165,047 A * | 12/2000 | Scott et al. | 450/55 |
| 6,213,842 B1 | 4/2001 | Degirmenci | |
| 6,234,867 B1 | 5/2001 | Fanelli | |
| 7,244,167 B2 * | 7/2007 | Falla | 450/54 |
| 7,413,495 B1 | 8/2008 | Sobah-Wilhelm | |
| 2005/0256572 A1 | 11/2005 | Wild | |

* cited by examiner

*Primary Examiner* — Gloria Hale
(74) *Attorney, Agent, or Firm* — Benoît & Côté Inc.

(57) ABSTRACT

The present document describes a prosthesis for a mastectomy bra comprising: a lower portion comprising a manually malleable material having a first density; and an upper portion comprising a manually malleable material having a second density smaller than the first density, the lower portion being substantially located below the upper portion thereby insuring stability of the prosthesis when in use. There is also described a bra for receiving the prosthesis.

16 Claims, 5 Drawing Sheets

MASTECTOMY PROSTHESIS AND BRA

TECHNICAL FIELD

This description relates to the field of bras. More particularly, this description relates to bras and prostheses adapted for women who underwent a mastectomy.

BACKGROUND

Women who have undergone a mastectomy of one or both breasts still want or need to wear a bra to mitigate, among other reasons, the psychological effect of the operation. Several types of prostheses and bras for mastectomy exist. Existing bras and matching prostheses are not necessarily fashionable or comfortable.

There is therefore a need for improved mastectomy prostheses and bras.

SUMMARY

According to an embodiment, there is provided a prosthesis for a mastectomy bra comprising: a lower portion comprising a manually malleable material having a first density; and an upper portion comprising another manually malleable material having a second density smaller than the first density, the lower portion being substantially located below the upper portion thereby insuring stability of the prosthesis when in use.

According to an embodiment, there is provided the prosthesis above wherein the lower portion comprises a lower compartment for receiving the manually malleable material having the first density and the upper portion comprises an upper compartment for receiving the other manually malleable material having the second density.

According to an embodiment, there is provided the prosthesis above further comprising a lower internal pouch for containing the manually malleable material having the first density.

According to an embodiment, there is provided the prosthesis above wherein the manually malleable material having the first density comprises a hydrocarbon gel.

According to an embodiment, there is provided the prosthesis above further comprising an upper internal pouch for containing the other manually malleable material having the second density.

According to an embodiment, there is provided the prosthesis above wherein the other manually malleable material having the second density comprises polystyrene microbeads.

According to an embodiment, there is provided the prosthesis above further comprising an upper internal pouch for containing the other manually malleable material having the second density.

According to an embodiment, there is provided the prosthesis above wherein the other manually malleable material having the second density comprises polystyrene microbeads.

According to an embodiment, there is provided the prosthesis above wherein the prosthesis comprises an outer shell for containing the lower portion and the upper portion.

According to an embodiment, there is provided the prosthesis above wherein the outer shell has a left shape adapted a left cup of the mastectomy bra and a right shape adapted a right cup of the mastectomy bra, the left and the right shapes being a mirror image of each other.

According to an embodiment, there is provided the prosthesis above further comprising a pre-formed foam portion inside the outer shell.

According to an embodiment, there is provided a mastectomy bra comprising a cup adapted for receiving a prosthesis, the prosthesis comprising a lower portion comprising a manually malleable material having a first density; and an upper portion comprising another manually malleable material having a second density smaller than the first density, the lower portion being located substantially below the upper portion thereby insuring stability of the prosthesis when in use.

According to an embodiment, there is provided a mastectomy bra comprising a cup substantially covering an area of a wearer's chest from which a breast was removed when the bra is worn, the cup comprising fabric material and a preformed material supported by the fabric material and for substantially maintaining a shape of the cup, the cup comprising a pocket for receiving a mastectomy prosthesis.

According to an embodiment, there is provided the bra above wherein the cup comprises an upper internal circumferential edge portion for substantially coming into contact with the wearer's chest whereby the cup thereby substantially covers the area of the wearer's chest from which the breast was removed According to an embodiment, there is provided the bra above further comprising a lower circumferential edge portion; and wherein each cup further comprises an apex, a ratio between a shortest distance from the apex to the upper circumferential edge portion and radial distance from the apex to the lower circumferential edge portion, the radial distance being opposite the shortest distance, being greater than 65%.

According to an embodiment, there is provided the bra above wherein the ratio is greater than at least one of 75%, 80%, 85%, 90% and 95%.

According to an embodiment, there is provided the bra above further comprising a lower circumferential edge portion comprising a portion which is reinforced with a wire.

According to an embodiment, there is provided the bra above wherein the preformed material comprises solid foam.

According to an embodiment, there is provided the bra above comprising two of said cup.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1A:
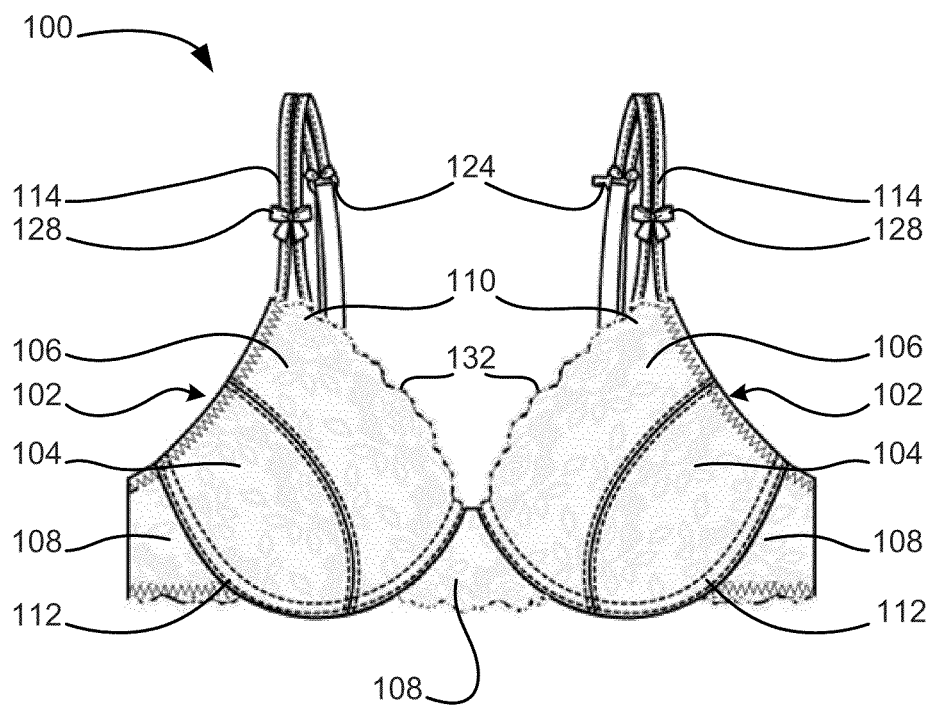
FIG. 1A is a front elevation view of a mastectomy bra in accordance with an embodiment.

Referring now to the drawings, and more particularly to FIG. 1, there is shown a bra 100 for women who underwent a mastectomy. The bra 100 comprises a pair of substantially symmetrical cups 102. The cups are either for supporting the remaining breast or for simulating the breast (or breasts) which has (have) been removed. The cups 102 are each made of two pieces of fabric 104 and 106 sewn together to obtain a breast shape. Lower edge 112 of each cup 102 is sewn to a band 108 for holding the bra on a user at breast level. Each of the lower edges 112 is reinforced with a wire for forming a rigid cradle to receive the remaining breast and to stress the form of the removed breast. The wire can be a strip of steel, or a strip or a rod of rigid plastic or of composite material.

Cups 102 are shaped for substantially or completely covering a portion of a wearer's chest corresponding to the area previously occupied by a breast. Each cup 102 has an upper internal circumferential edge portion 132 adapted for substantially coming into contact with the wearer's chest whereby the cup thereby substantially covers the original location of a breast on the chest.

The bra 100 further comprises two front straps 114 attached to upper portions 110 of the cups 102. Each front strap 114 links the upper portion 110 of one of the cups 102 to a ring 124. Front straps 114 run over the shoulders of the user. A decorative element 128 is put on each front strap 114.

Figure 1B:
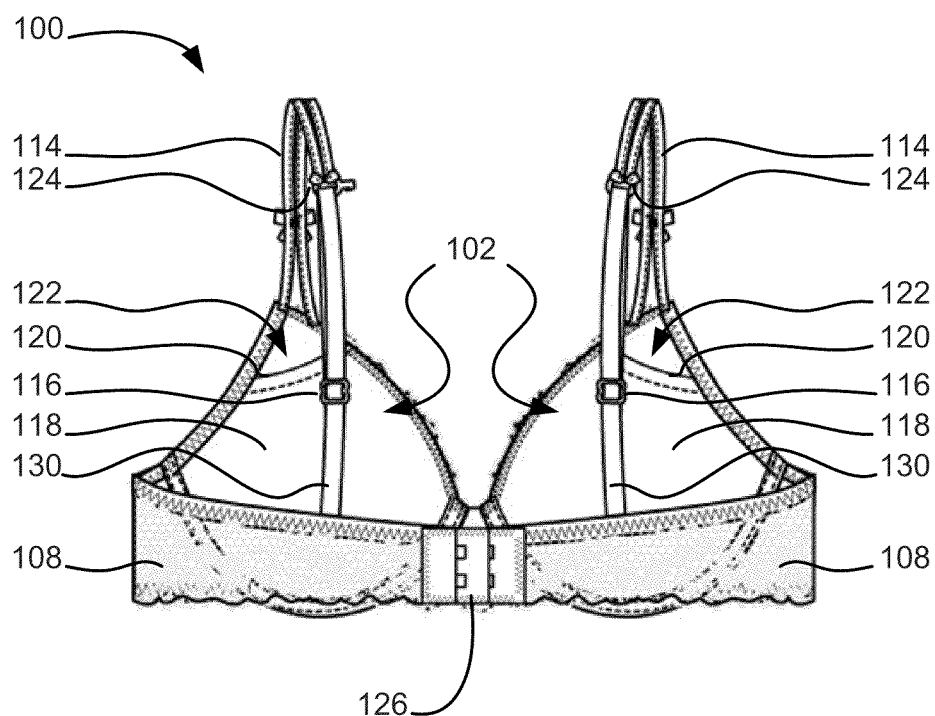
FIG. 1B is a rear elevation view of the mastectomy bra of FIG. 1.

Referring to FIG. 1B, there is shown the bra 100 seen from rear. A third piece of fabric 118 is partially peripherally and internally sewn to each cup 102. A free edge 120 of the third piece of fabric 118 forms an opening 122 of a pocket for introducing a prosthesis therein to simulate a real breast.

Rear straps 130 are sewn to the band 108, each corresponding to each of the front straps 114. Each rear strap 130 passes through the corresponding ring 124 fixed to the corresponding front strap 114 and runs back to a slider 116 for adjusting its length. The band 108 is detachable by a clasp 126. In another embodiment, the cup 102 corresponding to the remaining breast does not comprise the third piece of fabric 118 for better comfort.

According to another embodiment, the bra 100 optionally comprises a detachable back hook integrated to at least one of the rings 124. The back hook is for disconnecting and connecting to the opposite ring 124. The rear straps 130 may thereby create an X-effect to further adjust the bra.

According to another embodiment, the rear straps 130 cross. One of the rear straps 130 is sewn to a right portion of the band 108 and passes through the ring 124 of the left front strap 114. Symmetrically, the other rear strap 130 is sewn to a left portion of the band 108 and passes through the ring 124 of the right front strap 114. This creates an X-effect enhancing the maintaining of the straps, especially during physical exercises.

Figure 2A:
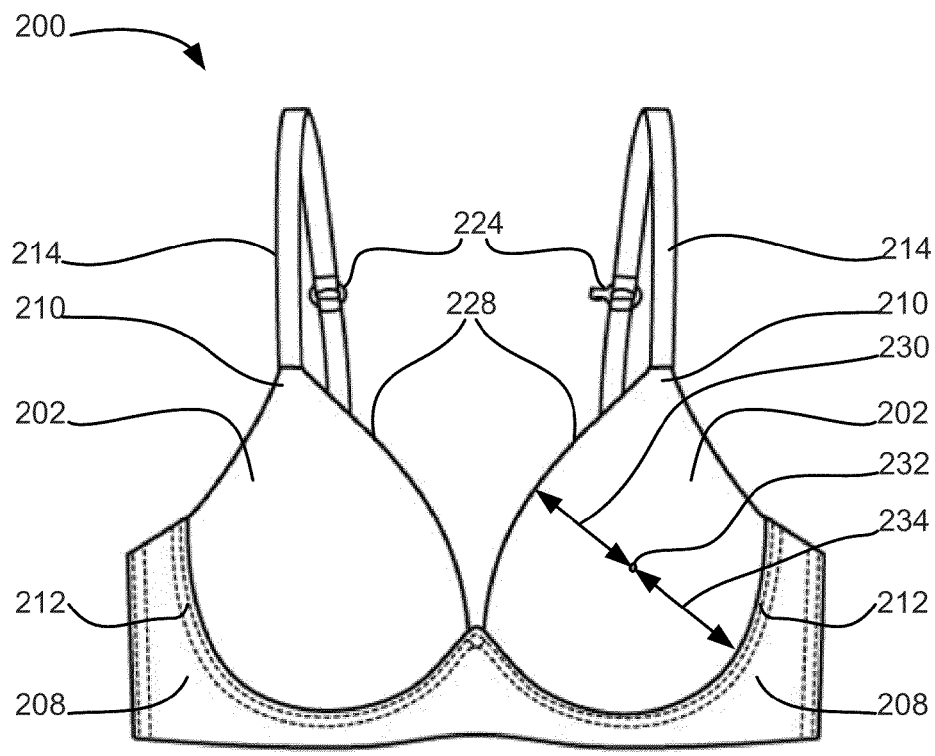
FIG. 2A is a front elevation view of a mastectomy bra in accordance with another embodiment.

Now referring to FIG. 2A, there is shown a mastectomy bra 200 according to another embodiment. The bra 200 comprises a pair of substantially symmetrical cups 202. Cups 202 are made of fabric material (i.e. a lining portion). The fabric material supports preformed material which substantially maintains a shape of each cup 202. According to an embodiment, the preformed material comprises solid foam having a significant portion of open cells to be sufficiently flexible to provide comfort. The preformed material can further comprise a lining and an inter-lining.

Each cup 202 comprises a lower circumferential edge portion 212 sown to a band 208. In the embodiment shown on FIGS. 2A and 2B, there is no reinforcement wire.

Cups 202 are shaped for covering a portion of a wearer's chest corresponding to the area previously occupied by a breast. Each cup 202 has an upper internal circumferential edge portion 228 adapted for substantially coming into contact with the wearer's chest whereby the cup thereby substantially covers the original location of a breast on the chest.

According to an embodiment, dimensions of such cups 202 can be defined by a ratio between a shortest distance 230 from an apex 232 to the upper circumferential edge portion 228 and a radial distance 234 from the apex 232 to the lower circumferential edge portion 212. The radial distance 234 is opposite the shortest distance 230. According to an embodiment, the defined ratio is greater than 65%. According to another embodiment, the ratio is greater than at least one of 75%, 80%, 85%, 90% and 95%.

The bra 200 further comprises two front straps 214 attached to upper portions 210 of the cups 202. Each front strap 214 links the upper portion 210 of one of the cups 202 to a ring 224. Front straps 214 run over the shoulders of the user.

Figure 2B:
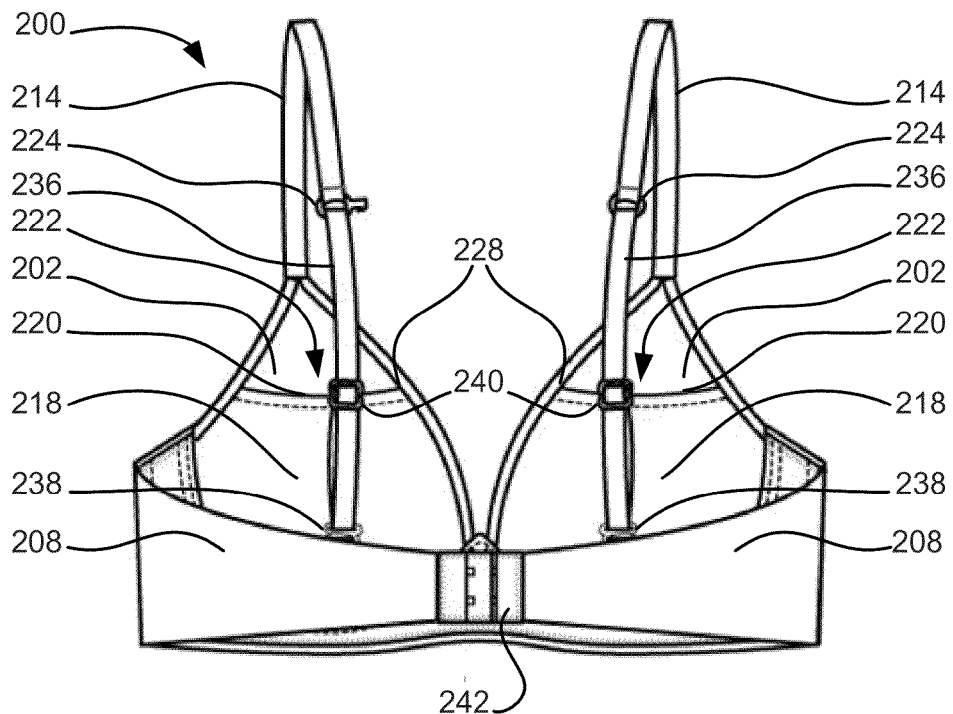
FIG. 2B is a rear elevation view of the mastectomy bra of FIG. 2.
Figure 3A:
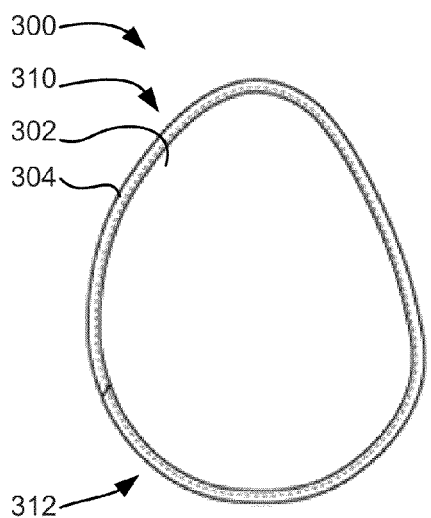
FIG. 3A is front elevation view of a right prosthesis for mastectomy bra in accordance with another embodiment.
Figure 3B:
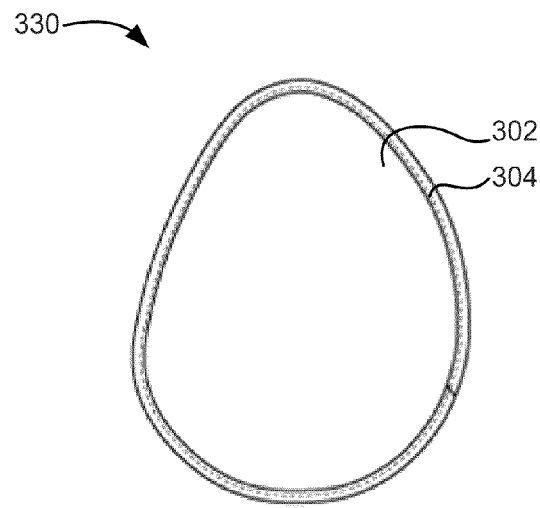
FIG. 3B is front elevation view of a left prosthesis according to the embodiment of FIG. 3A.
Figure 3C:
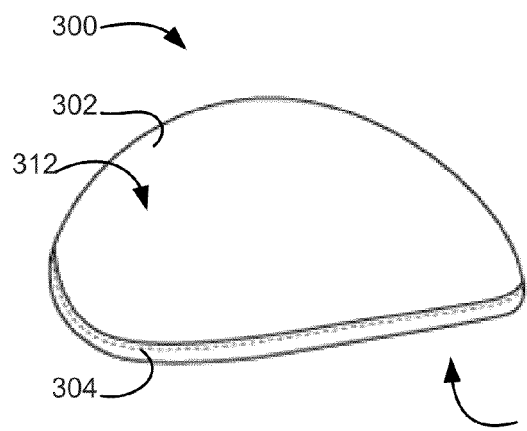
FIG. 3C is a perspective view of the right prosthesis of FIG. 3A seen from the right.
Figure 3D:
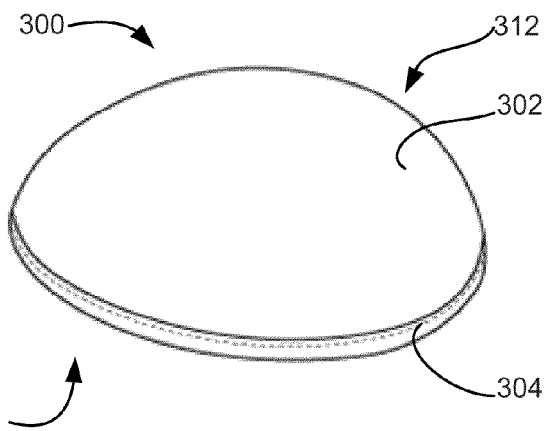
FIG. 3D is a perspective view of the right prosthesis of FIG. 3A seen from the left.

Referring to FIG. 2B, there is shown the bra 200 seen from rear. A piece of fabric 218 is partially peripherally and internally sewn to each cup 202. A free edge 220 of piece of fabric 218 forms an opening 222 of a pocket for introducing a prosthesis therein to give volume to a simulated breast.

In some cases, for sport practice for example, a wearer could prefer to limit the volume of her simulated breast. In these cases, a prosthesis of a different volume or weight can be introduced in the pocket.

One ring of back slides 238 is sewn to the band 208 on each side. Rear straps 236 are sewn to the rings 224, each corresponding to a respective one of the front straps 214. Each rear strap 236 passes through the corresponding back slide 238 and runs back to a slider 240 for adjusting its length. The band 208 is detachable by a clasp 242.

In another embodiment, the bra 200 optionally comprises a detachable back hook integrated to at least one of the rings 224. The back hook is for disconnecting and connecting to the opposite ring 224. The rear straps 236 may thereby create an X-effect to further adjust the bra.

In another embodiment, the rear straps 236 cross. One of the rear straps 236 is sewn to the ring 224 of the right front strap 214 and passes through the left back slide 238. Symmetrically, the other rear straps 236 is sewn to the ring 224 of the left front strap 214 and passes through the right back slide 238. This creates an X-effect enhancing the maintaining of the straps, especially during physical exercises.

Concurrently referring to FIG. 3A to FIG. 3D, there are shown different views of a right prosthesis 300 and a left prosthesis 330 which can be inserted in the bra 100 or the bra 200. The prosthesis 300 comprises an upper portion 310 and a lower portion 312. The prosthesis 300 has an outer shell 302 made of two pieces of fabric peripherally sown together and a shape 304 adapted for a right cup of a bra. The prosthesis 330 is adapted for a left cup and is a mirror image of the prosthesis 300. The prosthesis 300 is therefore differently shaped depending on whether it is for a left cup or a right cup.

Figure 4:
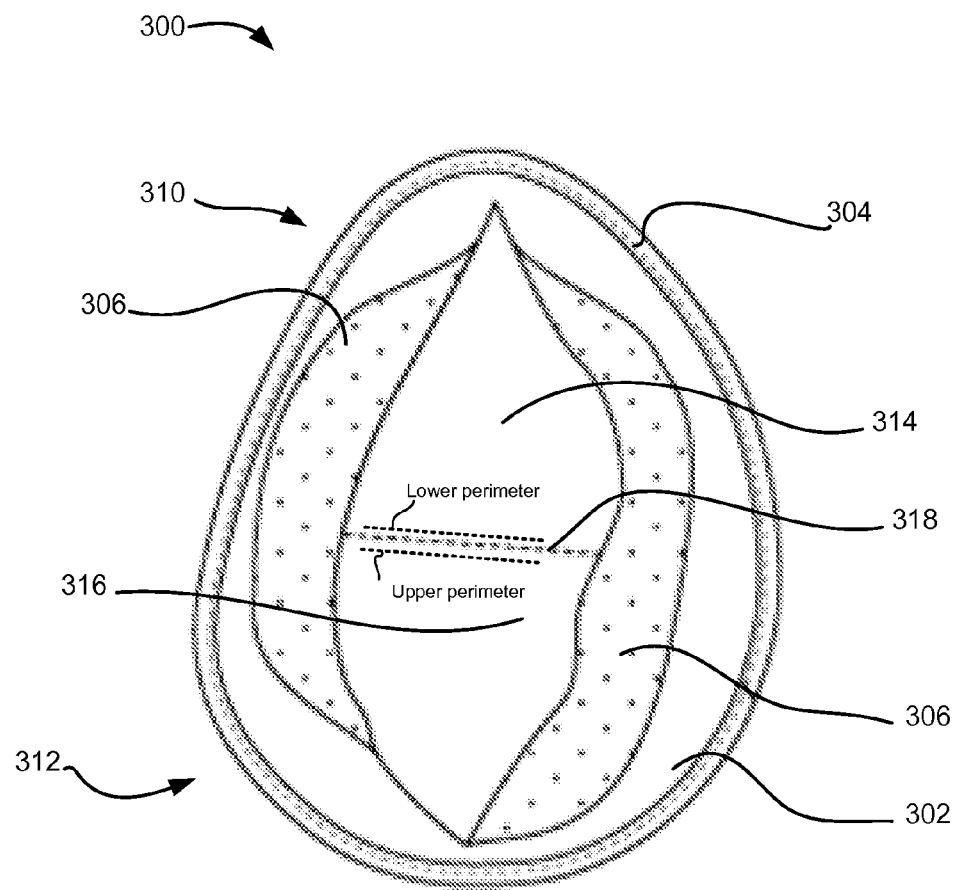
FIG. 4 is a rear elevation view of the right prosthesis of FIG. 3A which has been opened.

Referring to FIG. 4, there is shown a rear view of the prosthesis 300. The rear portion of the outer shell 302 has been cut to show the inside of the prosthesis. Two areas 306 are internal faces of the outer shell 302. Inside the outer shell 302 an additional piece of fabric forms an upper compartment 314 and a lower compartment 316 separated by an additional sewing 318. The upper compartment 314 is mostly in the upper portion 310 of the prosthesis 300 and the lower compartment 316 is mostly in the lower portion 312 of the prosthesis 300. The lower portion 312 comprises a manually malleable material having a first density, preferably comprising hydrocarbon gel. The upper portion 310 comprises a manually malleable material having a second density, preferably comprising polystyrene microbeads.

In use, the lower portion 312 is substantially located below the upper portion 310, thereby insuring stability of the prosthesis 300. Materials of the lower portion 312 and of the upper portion 310 are manually malleable to easily adapt the shape of the prosthesis 300 to the anatomy of the chest of the wearer.

Figure 5:
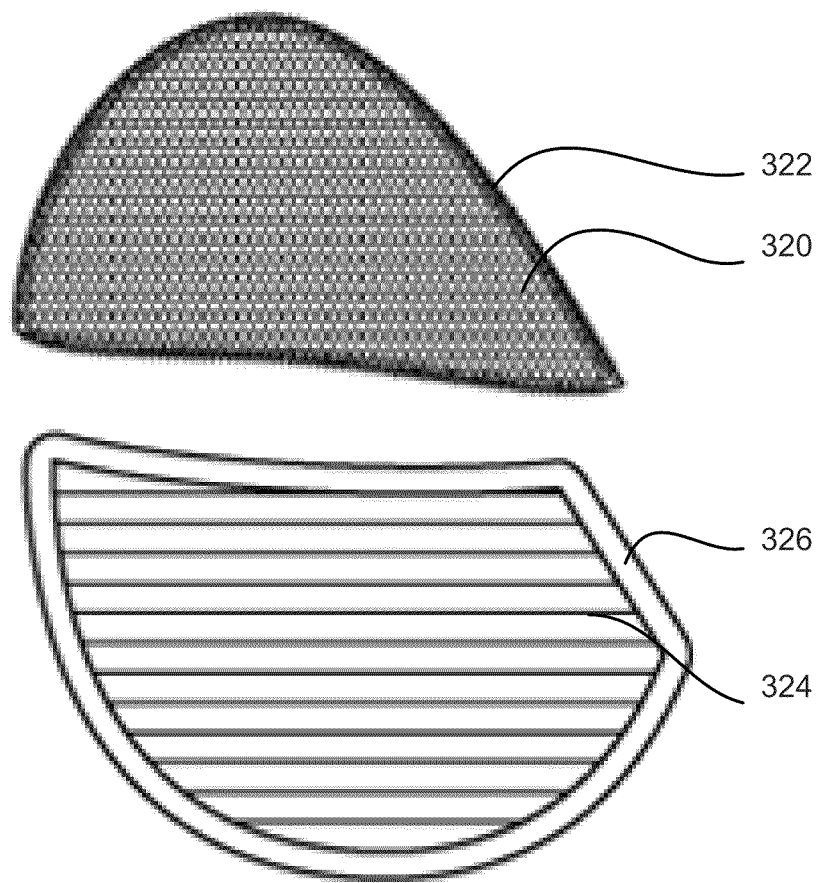
FIG. 5 is a front elevation view of an upper internal pouch and a lower internal pouch of the right prosthesis of FIG. 3A.

Ending with FIG. 5, there are shown an upper internal pouch 322 and a lower internal pouch 326 which are made for being respectively inserted in the upper compartment 314 and in the lower compartment 316 of the prosthesis 300. The upper internal pouch 322 and the lower internal pouch 326 are both made from a flexible material. The lower internal pouch 326 is closed and comprises the manually malleable material 324 having a first density. The upper internal pouch 322 is closed and comprises the manually malleable material 320 having a second density smaller than the first density. In use, the lower compartment 316 is located substantially below the upper compartment 314, thereby ensuring stability of the prosthesis 300.

While preferred embodiments have been described above and illustrated in the accompanying drawings, it will be evident to those skilled in the art that modifications may be made therein without departing from the essence of this disclosure. Such modifications are considered as possible variants comprised in the scope of the disclosure.

The invention claimed is:

1. A prosthesis for a mastectomy bra comprising:
   a first manually malleable material having a first density;
   a second manually malleable material having a second density lower than the first density;
   a lower compartment defining an upper perimeter for receiving the first manually malleable material having the first density; and
   an upper compartment defining a lower perimeter for receiving the second manually malleable material having the second density, the lower perimeter of the upper compartment being substantially above the upper perimeter of the lower compartment thereby ensuring stability of the prosthesis when in use in the mastectomy bra.

2. The prosthesis of claim 1, further comprising a lower internal pouch for containing the first manually malleable material having the first density; the lower compartment for receiving the lower internal pouch; an upper internal pouch for containing the second manually malleable material having the second density; and the upper compartment for receiving the upper internal pouch.

3. The prosthesis of claim 2, wherein the first manually malleable material having the first density comprises a hydrocarbon gel.

4. The prosthesis of claim 3, wherein the second manually malleable material having the second density comprises polystyrene microbeads.

5. The prosthesis of claim 2, wherein the second manually malleable material having the second density comprises polystyrene microbeads.

6. The prosthesis of claim 2, further comprising an outer shell for containing the lower compartment and the upper compartment.

7. The prosthesis of claim 6, wherein the outer shell has a left shape adapted for a left cup of the mastectomy bra and a right shape adapted for a right cup of the mastectomy bra, the left and the right shapes being a mirror image of each other.

8. The prosthesis of claim 6, further comprising a preformed foam portion inside the outer shell.

9. A mastectomy bra comprising:
   a prosthesis;
   a cup comprising a pocket to receive the prosthesis, the prosthesis being removable from the mastectomy bra;
   the prosthesis comprising:
      a first manually malleable material having a first density; and
      a second manually malleable material having a second density lower than the first density, the first manually malleable material being substantially located below the second manually malleable material thereby ensuring stability of the prosthesis when in use.

10. A mastectomy bra comprising a cup that when worn substantially covers an area of a wearer's chest where a wearer's breast was surgically removed, the cup further comprising a fabric material layer supporting a preformed material layer to thereby maintain a shape of the cup and with the cup further comprising a pocket to receive a mastectomy prosthesis therein, wherein the cup comprises an upper internal edge portion for substantially coming into contact with the wearer's chest whereby the cup thereby substantially covers the area of the wearer's chest from which the breast was removed, the mastectomy bra further comprising a lower edge portion adjacent the upper internal edge portion; and wherein each cup further comprises an apex, a ratio between a shortest distance from the apex to the upper internal edge portion and a radial distance from the apex to the lower circumferential edge portion being greater than 65%, the radial distance being opposite from and in the same direction as the shortest distance.

11. The bra of claim 10, wherein the ratio is greater than at least one of 75%, 80%, 85%, 90% and 95%.

12. The bra of claim 10, further comprising a lower edge portion comprising a portion which is reinforced with a wire.

13. The bra of claim 10, wherein the preformed material comprises solid foam.

14. The bra of claim 10, comprising two of said cup.

15. The mastectomy bra of claim 9, further comprising a lower compartment for receiving the first manually malleable material having the first density; and an upper compartment for receiving the second manually malleable material having the second density.

16. The mastectomy bra of claim 15, wherein the lower compartment defines an upper perimeter, wherein the upper compartment defines a lower perimeter and further wherein the lower perimeter of the upper compartment is being substantially above the upper perimeter of the lower compartment thereby ensuring stability of the prosthesis when in use in the mastectomy bra.

* * * * *